(12) United States Patent
Lee et al.

(10) Patent No.: US 9,535,499 B2
(45) Date of Patent: Jan. 3, 2017

(54) METHOD AND DISPLAY APPARATUS FOR PROVIDING CONTENT

(71) Applicant: SAMSUNG ELECTRONICS CO., LTD., Suwon-si (KR)

(72) Inventors: Jun-seok Lee, Seoul (KR); Sang-won Leigh, Yongin-si (KR); Sung-goo Cho, Seongnam-si (KR); Kyung-hwa Yu, Seoul (KR); Jin-yong Chung, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 172 days.

(21) Appl. No.: 13/943,957

(22) Filed: Jul. 17, 2013

(65) Prior Publication Data

US 2014/0022157 A1    Jan. 23, 2014

(30) Foreign Application Priority Data

Jul. 18, 2012 (KR) .......................... 10-2012-0078309

(51) Int. Cl.
*G06F 3/01*    (2006.01)
*G06F 3/0481*    (2013.01)

(52) U.S. Cl.
CPC .............. *G06F 3/015* (2013.01); *G06F 3/013* (2013.01); *G06F 3/0481* (2013.01); *G06F 2203/011* (2013.01); *G06F 2203/0381* (2013.01)

(58) Field of Classification Search
CPC ............. G06F 3/01; G06F 3/013; G06F 3/015
USPC ................................................. 345/175–177
See application file for complete search history.

(56) References Cited

U.S. PATENT DOCUMENTS

| 5,740,812 A * | 4/1998 | Cowan ............... A61B 5/04845 600/545 |
| 2004/0098193 A1 * | 5/2004 | Kageyama ............. G01C 21/26 701/408 |
| 2006/0252979 A1 * | 11/2006 | Vesely et al. ................... 600/27 |
| 2008/0065468 A1 * | 3/2008 | Berg ...................... G06Q 30/02 705/7.32 |
| 2009/0112656 A1 | 4/2009 | Jung et al. |
| 2009/0112849 A1 * | 4/2009 | Jung et al. ........................ 707/5 |

(Continued)

FOREIGN PATENT DOCUMENTS

| JP | 2006196995 A | 7/2006 |
| JP | 2007067739 A | 3/2007 |

(Continued)

OTHER PUBLICATIONS

Communication, dated Nov. 5, 2013, issued by the European Patent Office in counterpart European Application No. 13173882.5.

(Continued)

*Primary Examiner* — David Tung
(74) *Attorney, Agent, or Firm* — Sughrue Mion, PLLC (57) ABSTRACT

A method and display apparatus for providing content are provided. The method for providing content includes displaying a content UI in which a plurality of content is included, detecting an area at which a user gazes in the content UI, determining a preference for gaze content that is present in the area at which the user gazes by measuring user's brainwaves, and providing the content UI based on the determined preference. The user can be provided with the content UI that is configured more intuitively and conveniently according to the user preference.

19 Claims, 10 Drawing Sheets

(56) References Cited

U.S. PATENT DOCUMENTS

| | | | |
|---|---|---|---|
| 2009/0289895 A1* | 11/2009 | Nakada | G06F 3/015 345/157 |
| 2010/0191727 A1* | 7/2010 | Malik | 707/734 |
| 2011/0214082 A1 | 9/2011 | Osterhout et al. | |
| 2011/0254865 A1* | 10/2011 | Yee et al. | 345/661 |

FOREIGN PATENT DOCUMENTS

| | | | |
|---|---|---|---|
| JP | 2007156877 A | 6/2007 | |
| WO | 2004084054 A2 | 9/2004 | |

OTHER PUBLICATIONS

Communication dated Sep. 29, 2016, issued by the European Patent Office in counterpart European Application No. 13173882.5.
Office Action dated Nov. 8, 2016, and issued by Japanese Patent Office for Japenese Patent Application No. 2013-148223.

* cited by examiner

METHOD AND DISPLAY APPARATUS FOR PROVIDING CONTENT

PRIORITY

This application claims priority under 35 U.S.C. §119(a) to Korean Patent Application No. 10-2012-0078309 filed on Jul. 18, 2012, in the Korean Intellectual Property Office, the disclosure of which is incorporated herein by reference in its entirety.

BACKGROUND

1. Field

The inventive concept relates to a method and display apparatus for providing content. More particularly the present disclosure relates to a method and display apparatus, which can determine user preference for content using a user's brainwaves, and provide a content UI.

2. Description of the Related Art

Recently, with the continuing development of the Internet, the development of cultural industries, and the increase in the standards of education, the amount of content has rapidly increased, and various methods for providing content have been proposed. In particular, as the digital age draws near, intangible content transfer methods through the Internet have been popularized in addition to content transfer methods through tangible storage media, such compact discs (CDs), books, and newspapers.

As the amount of content increases, it gradually becomes difficult for a user to search for a user's preferential content. Display devices in related art provide content UIs regardless of user's preferential content. Further, even in the case where a user is able to directly set the user's preferential content, the user must set the user's preferential content one by one using an input device such as a mouse or a keyboard which is inconvenient to use.

Recently, in order to ascertain human judgment and feelings, research involving human brainwaves has been actively occurring. Specifically, in addition to the brainwaves reflecting movement of muscles around user's eyes the brainwaves also reflect the user's judgment and feelings. Through this measurement of brainwaves, performing data formation with respect to the measured brainwaves, and then again measuring the human brainwaves, the human judgment or feelings can be recognized through the measured brainwaves. Recently, research for use of brainwaves to ascertain a judgment of a user's feelings has been actively occurring.

Accordingly, in order to more conveniently and more intuitively provide user's preferential content, there has been a need for determining and providing user's preferential content through detection of the user's brainwaves.

SUMMARY

The inventive concept has been made to address at least the above problems and/or disadvantages and to provide at least the advantages described below. Accordingly, an aspect of the inventive concept provides a method and display apparatus for providing content, which can determine a preference for content upon which a user gazes by measuring the user's brainwaves and provide the content based on the preference determined by the brainwaves, to provide the content to which the user prefers more intuitively and conveniently.

According to one aspect of the inventive concept, a method for providing content of a display apparatus includes displaying a content UI in which a plurality of content is included; detecting an area in the content UI at which a user gazes; determining a preference from gaze content that is present in the area at which the user gazes by measuring the user's brainwaves; and providing the content UI based on the determined preference.

The providing step may provide as recommended content the content that is similar to the gaze content in response to the preference for the gaze content being equal to or higher than a predetermined value.

The providing step may increase a size of at least one of the gaze content and the content that is similar to the gaze content and display the content in response to the preference for the gaze content being equal to or higher than a predetermined value.

The method for providing content according to an aspect of the inventive concept may further include determining a preference for a plurality of areas in the content UI, wherein the providing step may display at least one of the gaze content and the content that is similar to the gaze content in the area having a high preference in the content UI in response to the preference for the gaze content being equal to or higher than a predetermined value.

The providing step may display the at least one of the gaze content and the content that is similar to the gaze content in the area having low preference in the content UI in response the preference for the gaze content being lower than the predetermined value.

The providing step may delete or decrease a size of at least one of the gaze content and the content that is similar to the gaze content and display the content in response to the preference for the gaze content being lower than a predetermined value.

The detecting step may detect the area at which the user gazes by tracking at least one of a face direction and movement of a pupil of the user.

If the display apparatus is a 3D display apparatus, the brainwaves of the user may be measured using a brainwave measurer which is attached to 3D glasses that interlock with the 3D display apparatus.

According to another aspect of the inventive concept, a display apparatus includes a displayer which displays a content UI in which a plurality of content is included; a gaze area detector which detects an area at which a user gazes in the content UI; a brainwave measurer which measures user's brainwaves; and a controller which determines a preference for gaze content that is present in the area at which the user gazes by using the user's brainwaves measured by the brainwave measurer, and controlling the displayer to provide the content UI based on the determined preference.

The controller may provide content that is similar to the gaze content as recommended content in response to the preference for the gaze content being equal to or higher than a predetermined value.

The controller may increase a size of at least one of the gaze content and the content that is similar to the gaze content and may display the content in response to the preference for the gaze content being equal to or higher than a predetermined value.

The controller may determine a preference for a plurality of areas in the content UI, and may control the displayer to display at least one of the gaze content and the content that is similar to the gaze content in the area having high preference in the content UI in response to the preference for the gaze content being equal to or higher than a predetermined value.

The controller may control the displayer to display the at least one of the gaze content and the content that is similar to the gaze content in the area having low preference in the content UI in response to the preference for the gaze content being lower than the predetermined value.

The controller may control the displayer to delete or decrease a size of and display at least one of the gaze content and the content that is similar to the gaze content and display the content in response to the preference for the gaze content being lower than a predetermined value.

The gaze area detector may detect the area at which the user gazes by tracking at least one of a face direction and movement of a pupil of the user.

If the display apparatus is a 3D display apparatus, the brainwave measurer may be attached to 3D glasses that interlock with the 3D display apparatus.

BRIEF DESCRIPTION OF THE DRAWINGS

The above and other aspects, features and advantages of the inventive concept will be more apparent from the following detailed description when taken in conjunction with the accompanying drawings, in which.

DETAILED DESCRIPTION OF EXEMPLARY EMBODIMENTS

Hereinafter, exemplary embodiments of the inventive concept are described in detail with reference to the accompanying drawings.

Figure 1:
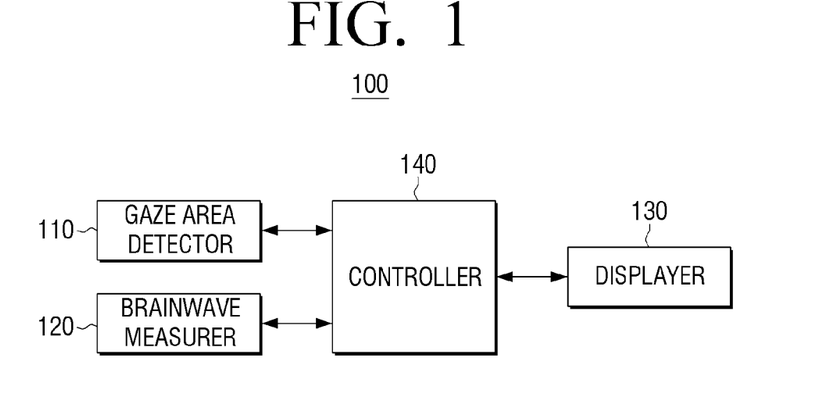
FIG. 1 is a block diagram schematically illustrating the configuration of a display apparatus according to an exemplary embodiment of the inventive concept.

FIG. 1 is a block diagram schematically illustrating the configuration of a display apparatus 100 according to an exemplary embodiment of the inventive concept. As illustrated in FIG. 1, a display apparatus 100 includes a gaze area detector 110, a brainwave measurer 120, a displayer 130, and a controller 140. The display apparatus 100 according to an exemplary embodiment of the inventive concept may be implemented in a smart TV. However, this is merely exemplary, and the display apparatus 100 may be implemented as various devices, such as a desk top PC, a tablet PC, a smart phone, etc.

The gaze area detector 110 detects an area at which a user gazes in the displayer 130. At this time, the gaze area detector 110 may detect the area at which the user gazes by tracking a face direction of the user or by tracking the movement of a user's eyeball.

The brainwave measurer 120 measures the user's brainwaves using a plurality of brainwave sensing electrodes. At this time, since the brainwave measurer 120 is required to be in contact with the user's face to measure the user's brainwaves, it may be implemented separately from the display apparatus 100. Particularly, in response to the display apparatus 100 being a 3D display apparatus, the brainwave measurer 120 may be attached to 3D glasses that interlock with the 3D display apparatus.

The displayer 130 displays a content UI that includes a plurality of content. The content UI may be a content list which includes a plurality of icons that correspond to the plurality of contents, but is not limited thereto.

Further, the displayer 130 may configure the content UI according to a user preference, under the control of the controller 140.

The controller 140 determines the preference for gaze content that is present in the area at which the user gazes using the brainwaves of the user measured by the brainwave measurer 120. Then, the controller 140 controls the displayer 130 to provide the content UI based on the determined preference.

Specifically, in response to the preference for the gaze content being equal to or higher than a predetermined value, the controller 140 may recommend content that is similar to the gaze content. At this time, the content that is similar to the gaze content may be content of which at least one of a title, a genre, a hero, a director and a production company coincides with that of the gaze content.

Further, in response to the preference for the gaze content being equal to or higher than the predetermined value, the controller 140 may control the displayer 140 to increase the sizes of and display the gaze content and the content that is similar to the gaze content.

However, in response to the preference for the gaze content being lower than the predetermined value, the controller 140 may control the displayer 130 to delete or decrease the size of the gaze content and display the content that is similar to the gaze content.

Further, the controller 140 may determine the preference for a plurality of areas in the content UI. In response to the preference for the gaze content being equal to or higher than the predetermined value, the controller 140 may control the displayer 130 to display the gaze content and the similar content in the area having high preference in the content UI.

However, in response to the preference for the gaze content being lower than the predetermined value, the controller 140 may control the displayer 130 to display the gaze content and the similar content in the area having low preference in the content UI.

As described above, by detecting the user preference of the content at which the user gazes, by measuring the user's brainwaves and providing the content UI according to the user preference, the user can be provided with the content UI that is more intuitively and conveniently configured according to the user preference.

Figure 2:
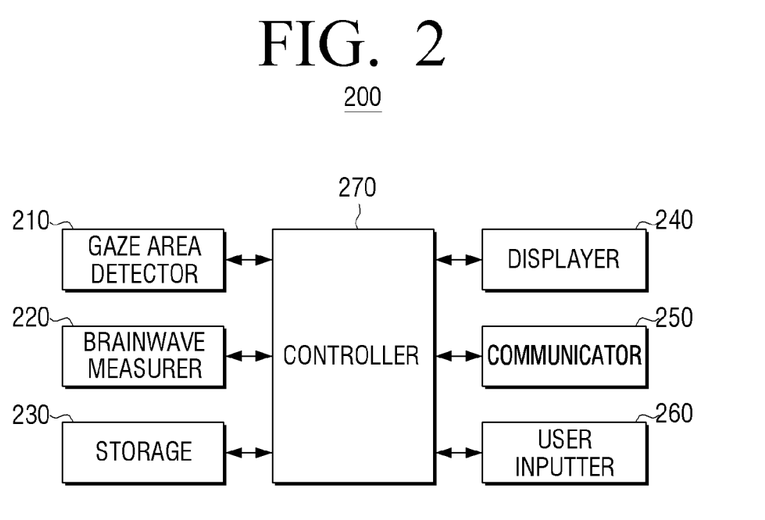
FIG. 2 is a block diagram illustrating the detailed configuration of a display apparatus according to another exemplary embodiment of the inventive concept.

Hereinafter, referring to FIGS. 2 to 8, the display apparatus will be described in more detail. FIG. 2 is a block diagram illustrating the detailed configuration of a display apparatus 200 according to another exemplary embodiment of the inventive concept. As illustrated in FIG. 2, a display apparatus 200 includes a gaze area detector 210, a brainwave measurer 220, a storage 230, a displayer 240, a communicator 250, a user inputter 260 and a controller 270.

The gaze area detector 210 detects an area at which a user gazes in a display screen. In particular, the gaze area detector 210 may detect the area at which the user gazes by tracking the movement of a user's eyeball.

Specifically, the gaze area detector 210 identifies an eyeball image from a user image photographed by a photographer (not illustrated) through a face modeling technique. At this time, the face modeling technique corresponds to an analysis procedure to process the face image acquired by the photographer and to convert the face image into digital information for transmission, and one of an ASM (Active Shape Modeling) technique and an AAM (Active Appearance Modeling) technique may be used as the face modeling technique. Here, the ASM technique is a model that detects feature points of a face region by first detecting positions of eyes in the face region and determining positions of other regions (for example, a nose, a mouth, eyebrows, and the like) using shape information of the other regions according to a generic model. The AAM technique is a model that detects feature points that can efficiently explain the face feature in further consideration of texture information in addition to the shape information.

The gaze area detector 210 may determine the movement of an eyeball using the identified eyeball image. Further, the gaze area detector 210 can determine the area at which the user gazes by detecting the direction in which the user gazes using the movement of the eyeball and comparing with each other the detected direction in which the user gases and pre-stored coordinate information of the display screen with each other.

Figure 10A:
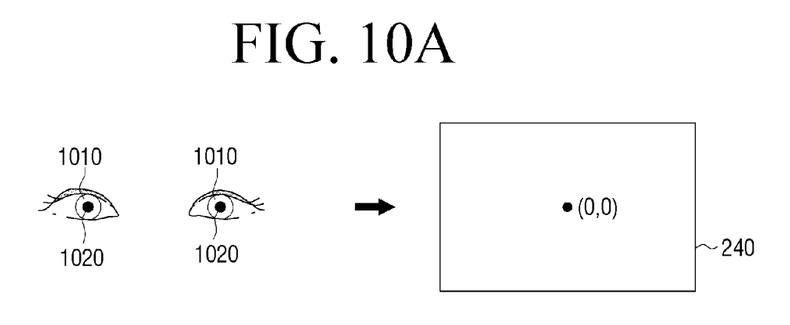
FIGS. 10A to 10C are diagrams illustrating a method for determining a display apparatus at which a user gazes according to an exemplary embodiment of the inventive concept.
Figure 10B:
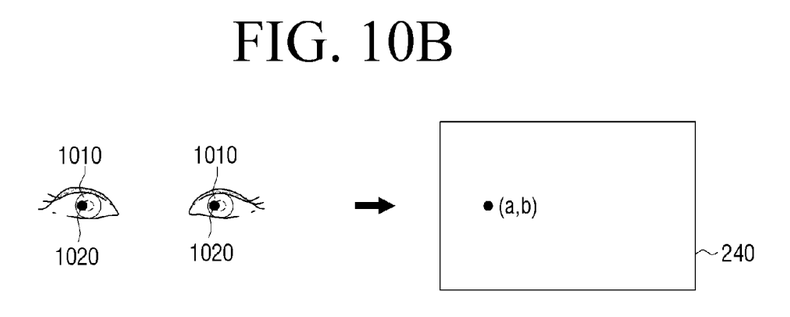
Figure 10C:
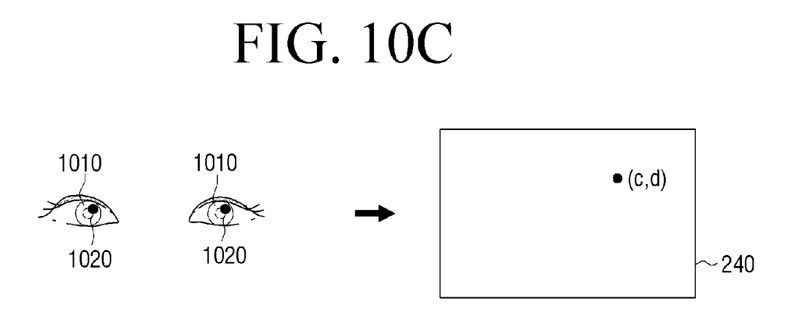

For example, as illustrated in FIG. 10A, in response to a determination that the pupil 1020 of the user, which is photographed based on pre-stored image information of an iris 1010 and the pupil 1020 of the user, is positioned in the center, the gaze area detector 210 may determine that the user gazes at the center (0, 0) of the display screen. Further, as illustrated in FIG. 10B, if it is determined that the pupil 1020 of the user has moved from the center to the left, the gaze area detector 210 may calculate a coordinate point (a, b) of the display screen, depending on the moving distance of the pupil 1020 of the user, and may determine that the user is gazing the point that has the calculated coordinate point. Further, as illustrated in FIG. 10C, in response to a determination that the pupil 1020 of the user has moved from the center to the upper right, the gaze area detector 210 may calculate a coordinate point (c, d) of the display screen depending on the movement of the pupil 1020 of the user, and may determine that the user is gazing at the point that has the calculated coordinate point.

However, the method for determining the area at which the user gazes as described above is merely exemplary, and it is possible to gaze the area at which the user gazes using other methods. For example, the gaze area detector 210 may determine the area at which the user gazes by tracking the direction of the user's face.

The brainwave measurer 220 measures the user's brainwaves from a plurality of brainwave sensing electrodes. In particular, since the brainwave measurer 120 is required to be attached to the user's head to measure the user's brainwaves, the brainwave measurer may be implemented separately from the display apparatus 100.

Figure 3:
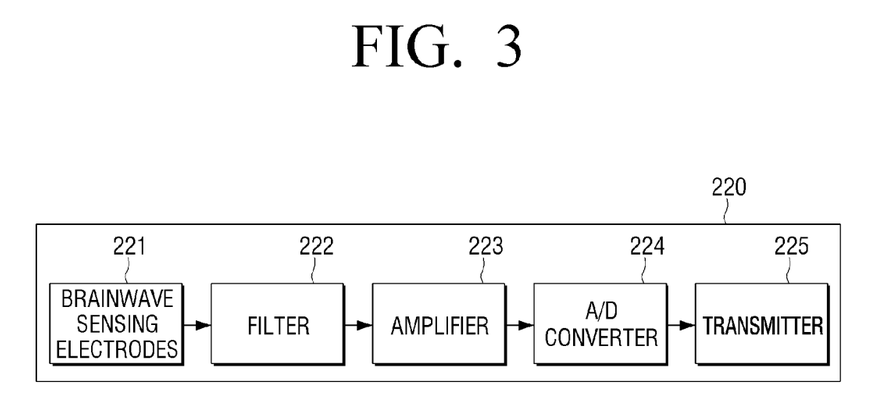
FIG. 3 is a block diagram illustrating the configuration of a brainwave detector according to an exemplary embodiment of the inventive concept.

The brainwave measurer 220 will be described in detail with reference to FIG. 3. As illustrated in FIG. 3, the brainwave measurer 220 includes a brainwave sensing electrode 221, a filter 222, an amplifier 223, an A/D converter 224, and a transmitter 225. The brainwave sensing electrode 221 is arranged on the outside of the brainwave detector 220 to sense the user's brainwaves. Particularly, in response to the brainwave detector 220 being included in 3D glasses, the brainwave sensing electrode 221 is arranged on a glass leg or a forehead contact portion of the 3D glasses in order to sense the user's brainwaves. At this time, the brainwave sensing electrode 221 includes at least one of an alpha electrode that detects the brainwaves in the range of 8 to 13 Hz, a beta electrode that detects the brainwaves in the range of 13 to 30 Hz, a gamma electrode that detects the brainwaves in the range of 30 to 50 Hz, a delta electrode that detects the brainwaves in the range of 0 to 4 Hz, and a theta electrode that detects the brainwaves in the range of 4 to 8 Hz, depending on the frequencies of the brainwaves.

The filter 222 filters the brainwaves sensed by the brainwave sensing electrode 221 and outputs the filtered brainwaves to the amplifier 223. At this time, the filter 222 may be implemented as a low pass filter (LPF), but, is not limited thereto. The amplifier 223 amplifies and outputs the brainwaves filtered by the filter 222 to the A/D converter 224. The A/D converter 224 converts the amplified brainwave information from an analog signal to a digital signal. The transmitter 225 transmits the brainwaves which are converted into the digital signal, to a main body of the display apparatus 200. At this time, the transmitter 225 may be implemented using a Wi-Fi® module or an IR module, but is not limited thereto.

The storage 230 stores various data and programs for driving the display apparatus 200. In particular, the storage 230 stores the brainwave information in the form of a histogram or matrix, which is mapped on the user preference. For example, the storage 230 may store first brainwave information that is mapped on "high preference," second brainwave information that is mapped on "middle preference," and third brainwave information that is mapped on "low preference." However, as described above, the three-level preference is merely exemplary, and a plurality of preference levels that are mapped on the brainwave information may be stored in addition to the three preference levels.

The displayer 240 displays image data under the control of the controller 270. In particular, the displayer 240 may display a content UI in which a plurality of content is included. At this time, the content UI may be a content list that includes icons which correspond to the plurality of content, but is not limited thereto. Further, the plurality of content may include movie content, broadcasting content, music content, photograph content, advertisement content, etc., but is not limited thereto.

The displayer 240 may configure the content UI according to the user preference under the control of the controller 270. The details of this will be described later with reference to FIGS. 4 to 8.

The communicator 250 communicates with an external device or a server; and may receive content information from the external device or the server.

On the other hand, the communicator may be implemented by a wireless communication module that is connected to an external network to perform communications according to wireless communication protocols, such as Wi-Fi® and IEEE®. In addition, the wireless communication module may further include a mobile communication module that is connected to a mobile communication network to perform communications according to various mobile communication standards, such as 3G® ($3^{rd}$ Generation), 3GPP® ($3^{rd}$ Generation Partnership Project), and LTE® (Long Term Evolution).

The user inputter 260 receives a user command for controlling the display apparatus 200. At this time, the user inputter 260 may be implemented by various input devices, such as a remote controller, a mouse, a keyboard and a touch screen.

The controller 270 controls the overall operation of the display apparatus 200 according to the user command input through the user inputter 260. In particular, the controller 270 determines the preference of the gaze content that is present in the area at which the user gazes using the user's brainwaves measured by the brainwave measurer 220. Further, the controller 270 controls the displayer 240 to provide the content UI based on the determined preference.

Figure 4:
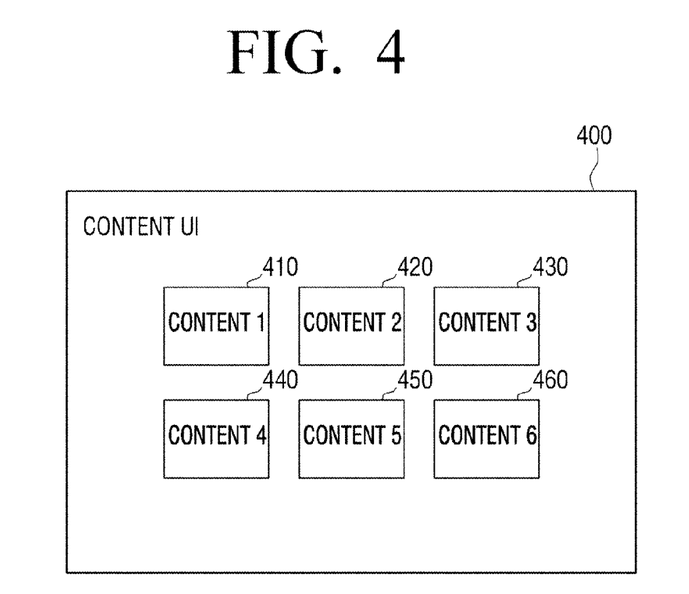
FIGS. 4 to 8 are diagrams illustrating content UIs configured on the basis of user preference according to various exemplary embodiments of the inventive concept.

Specifically, the controller 270 controls the displayer 240 to display the content UI (User Interface) in which the plurality of content transmitted from the outside through the communicator 250 is included. For example, as illustrated in FIG. 4, the controller 270 may control the displayer 240 to display the content UI 400 in which first content to sixth content 410 to 460 are included.

The controller 270 determines the content at which the user gazes through the gaze area detector 210. Specifically, the controller 270 may acquire coordinate information of the area at which the user gazes through the gaze area detector 210 and may determine the gaze content at which the user gazes in the content UI that is currently displayed using the coordinate information of the area at which the user gazes.

Further, in response to the user's brainwave information being transmitted from the brainwave measurer 220, the controller 270 determines the preference of the gaze content based on the user's brainwave information transmitted from the brainwave measurer 220. Specifically, in response to the user's brainwave information being transmitted from the brainwave measurer 220, the controller 270 processes the brainwave information in the form of a histogram or a matrix. Then, the controller 270 searches for the brainwave information pre-stored in the storage 230 to determine whether there exists the brainwave information that coincides with the processed user's brainwave information. If pre-stored brainwave information that coincides with the processed user's brainwave information is located as the result of search, the controller 270 determines the preference of the content at which the user gazes, using the user preference which matches the pre-stored brainwave information that coincides with the user's brainwave information. In a case where the processed user's brainwave information and the pre-stored brainwave information coincide with each other, this includes not only a case where the currently received brainwave information and the pre-stored brainwave information completely coincide with each other, but also a case where the currently received brainwave information and the pre-stored brainwave information are present within a predetermined error range.

Although the preference of the gaze content can be determined using the user's brainwave information that is stored, to match the user preference of the plurality of levels as described above, this is merely exemplary, and the preference of the gaze content can be determined using the user's brainwaves according to other methods. For example, in response to the brainwaves of a specified frequency being detected to a great extent from among the brainwave information, the controller 270 may determine the user preference of the gaze content, depending upon the specified frequency of the brainwaves.

Further, the preference of the gaze content of the user can not only be determined by using the pre-stored user's brainwave information but also by obtaining the user's brainwave information. For example, in the case of viewing specified content for a long period of time after the brainwaves of the specified frequency are detected, except for the pre-stored frequency, the controller 270 may store the newly detected brainwave information of the specified frequency that matches a high preference. Accordingly, in response to the brainwaves of the specified frequency being detected while the user gazes at certain content for a period of time, the controller 270 may determine that the user preference is high for the certain content.

In response to the preference being determined, the controller 270 may store the gaze content and the preference in the storage 230 and may provide the content UI according to the preference.

Figure 5:
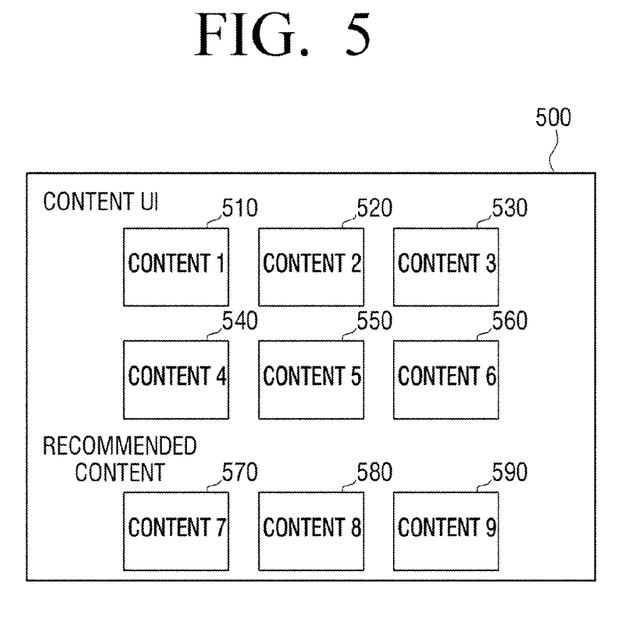

Specifically, in response to the preference of the gaze content being equal to or higher than a predetermined value, the controller 270 may recommend content that is similar to the gaze content. For example, in response to a determination that the gaze content is "content 1" 410 and the preference of the "content 1" is "high preference," the controller 270, as illustrated in FIG. 5, may provide, as the recommended content, "content 7" 570, "content 8" 580, and "content 9," which represents content similar to the gaze content, to the predetermined area in the content UI.

At this time, the content similar to the gaze content may be content of which at least one of a title, a genre, a hero, a director and a production company coincides with that of the gaze content.

Figure 6:
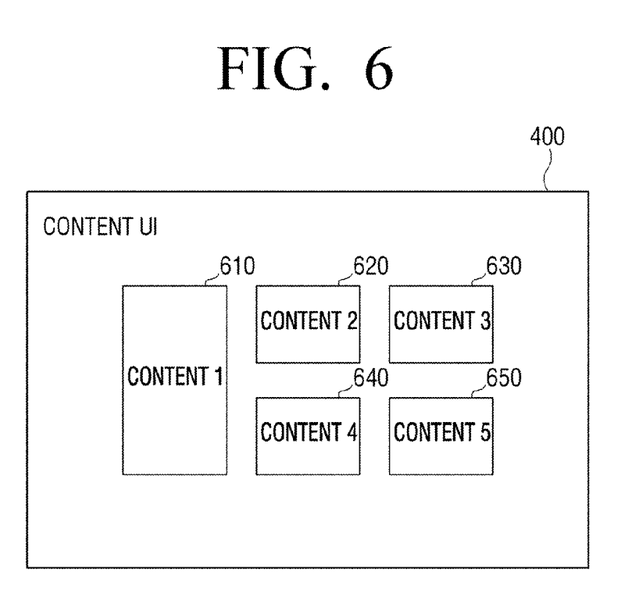

Further, in response to the preference for the gaze content being equal to or higher than the predetermined value, the controller 270 may increase the size of at least one of the gaze content and the content that is similar to the gaze content, and may display the content. For example, in response to a determination that the gaze content is "content 1" 410 and the preference of the "content 1" is "high preference", the controller 270, as illustrated in FIG. 6, may increase the size of and display "content 1" 610 which is the gaze content. On the other hand, although FIG. 6 shows that only the gaze content is displayed with an increased size, this is merely exemplary, and the content that is similar to the gaze content may also be displayed with an increased size.

Further, the controller 270 may determine the preference for a plurality of areas in the content UI. Specifically, in response to the user gazing at the plurality of areas in the content UI, the controller 270 may measure the user preference for an area among the plurality of areas, by measuring the user's brainwaves. For example, the controller 270 may divide the content UI into six areas (left upper, upper center, right upper, left lower, lower center, and right lower areas), and may determine the area having highest user preference, and may determine the area having lowest user preference through examination of the preference for each area.

Figure 7:
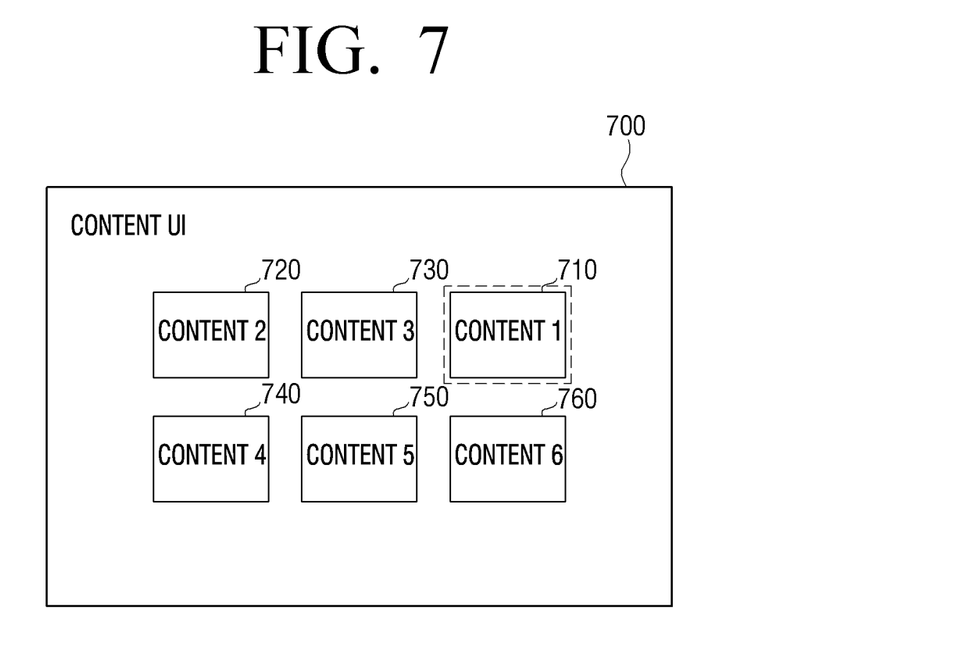

Further, in response to the preference for the gaze content being equal to or higher than the predetermined value, the controller 270 may display at least one of the gaze content and the content that is similar to the gaze content within the area having a high preference in the content UI. For example, in response to a determination that the user preference area is the "right upper" area, the gaze content is "content 1" 410, and the preference of the "content 1" is "high preference," the controller 270, as illustrated in FIG. 7, may control the displayer 240 to display the "content 1" 710 that is the gaze content in the right upper area of the content UI 700.

Further, in response to the preference for the gaze content being lower than the predetermined value, the controller 270 may display at least one of the gaze content and the content that is similar to the gaze content in the area having low preference in the content UI. For example, in response to a determination that the user preference area is the "left lower" area, the gaze content is "content 2" 420, and the preference of the "content 2" is "low preference," the controller 270 may control the displayer 240 to display the "content 2" which is the gaze content in the right left lower area of the content UI.

Figure 8:
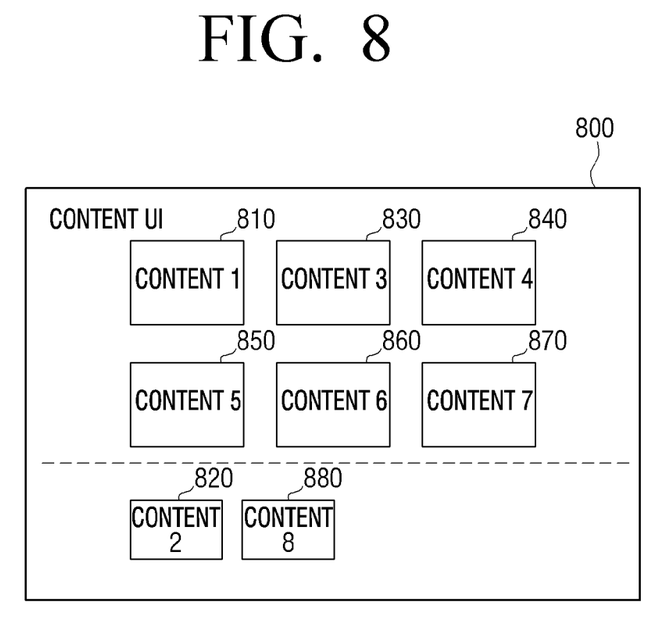

Further, in response to the preference for the gaze content being lower than the predetermined value, the controller 270 may delete or decrease the size of at least one of the gaze content and the content that is similar to the gaze content, and may display the gaze content. For example, in response to a determination that the gaze content is the "content 2" 420 and the preference of the "content 2" is "low preference," the controller 270, as illustrated in FIG. 8, may decrease the size of the "content 2" 820 that is the gaze content and the "content 8" 880 that is the content similar to the "content 2" 820 in the lower area of the content UI 800, and may display the content. However, although the size of the content, having the preference that is lower than the predetermined value, is reduced as illustrated in FIG. 8, this is merely exemplary. An embodiment in which the content having the preference that is lower than the predetermined value is deleted may be included in the technical features of the inventive concept.

In the above-described exemplary embodiment, the controller 270 reconfigures the content UI just after determining the preference of the gaze content. However, this is merely exemplary, and it is also possible to map and store the gaze content and the preference of the gaze content after the preference of the gaze content is determined, as well as to generate the content UI by reflecting the preference of the gaze content when a new content UI is generated at a later time.

As described above, by determining the user preference through measurement of the user's brainwaves and providing a content UI in which the user preference is reflected, the user can be provided with a content UI that is more intuitively and conveniently configured according to the user preference.

Figure 9:
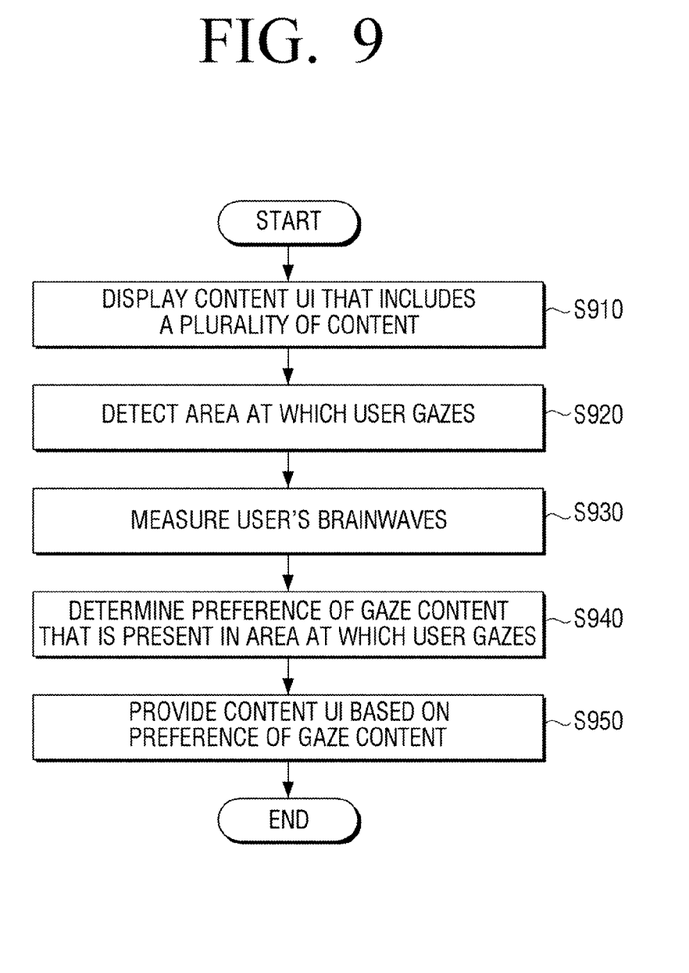
FIG. 9 is a flowchart illustrating a method for providing content according to an exemplary embodiment of the present disclosure.

Hereinafter, referring to FIG. 9, a method for providing content of the display apparatus 100 will be described.

The display apparatus 100 displays a content UI in which a plurality of content is included (S910). The content UI may be a content list that includes icons which correspond to the plurality of content. The plurality of content may include at least one of movie content, broadcasting content, music content and advertisement content.

Then, the display apparatus 100 detects the area at which the user gazes (S920). Specifically, the display apparatus 100 may photograph the user's face, and then detect the area at which the user gazes by tracking the movement of the user's eyeball.

The display apparatus 100 measures the user's brainwaves with respect to the area at which the user gazes using the brainwave measurer 120 (S930). At this time, in response to the display apparatus 100 being a 3D display apparatus, the brainwave measurer 120 may be attached to 3D glasses that interlock with the 3D display apparatus.

Further, the display apparatus 100 determines the preference for the gaze content that is present in the area at which the user gazes (S940). Specifically, the display apparatus 100 may determine the preference of the gaze content at which the user gazes by analyzing measured brainwaves of the user. At this time, the display apparatus may determine the preference of the gaze content that is configured at a plurality of levels.

Then, the display apparatus 100 provides the content UI based on the preference of the gaze content (S950). Specifically, in response to the preference for the gaze content being equal to or higher than the predetermined value, the display apparatus 100 may recommend content that is similar to the gaze content. At this time, the content that is similar to the gaze content may be content of which at least one of a title, a genre, a hero, a director and a production company coincides with that of the gaze content. Further, in response to the preference for the gaze content being equal to or higher than the predetermined value, the display apparatus 100 may increase the sizes of the gaze content and the content that is similar to the gaze content, and may display the gaze content. However, in response to the preference for the gaze content being lower than the predetermined value, the display apparatus 100 may delete or decrease the size of the gaze content and the content that is similar to the gaze content and may display the content.

Further, the display apparatus 100 may determine the preference for a plurality of areas in the content UI, and display the gaze content of one of the plurality of areas according to the preference of the gaze content. Specifically, in response the preference for the gaze content being equal to or higher than the predetermined value, the display apparatus 100 may display the gaze content and the content that is similar to the gaze content in the area having high preference in the content UI. However, in response to the preference for the gaze content being lower than the predetermined value, the display apparatus 100 may display the gaze content and the content that is similar to the gaze content in the area having low preference in the content UI.

As described above, by detecting the user preference of the content at which the user gazes by measuring the user's brainwaves and providing the content UI according to the user preference, the user can be more intuitively and conveniently provided with the content UI that is configured according to the user preference.

Program codes for performing the method for providing content according to various exemplary embodiments as described above may be stored in a non-transitory computer readable medium. The non-transitory computer readable medium means a device-readable medium which does not store data for a short time, such as a register, a cache, and a memory, but semi-permanently stores the data. Specifically, the above-described various applications or programs may be provided and stored in the non-transitory computer readable medium, such as a CD, a DVD, a hard disc, a Blu-ray Disc®, a USB, a memory card, and a ROM.

While the present disclosure has been shown and described with reference to certain exemplary embodiments thereof, it will be understood by those skilled in the art that various changes in form and detail may be made therein without departing from the spirit and scope of the present disclosure, as defined by the appended claims.

What is claimed is:
1. A method for providing content of a display apparatus, the method comprising:
  detecting an area at which a user gazes in a content user interface (UI);
  measuring brainwaves of the user with respect to the detected area at which the user gazes;

determining a preference for gaze content that is present in the detected area at which the user gazes based on the measured brainwaves of the user;

providing the gaze content with a changed size or position based on the determined preference, wherein the determining comprises:

determining whether there are pre-stored brainwaves coinciding with the measured brainwaves; and in response to the determining that there are pre-stored brainwaves coinciding with the measured brainwaves, determining, as the preference for the gaze content, a user preference matching the pre-stored brainwaves; and in response to the user viewing specified content for a long period of time after brainwaves of a specified frequency are detected, except for a pre-stored frequency, storing the detected brainwaves of the specified frequency that match a high preference.

2. The method for providing content as claimed in claim 1, further comprising recommending content that is similar to the gaze content in response to the preference for the gaze content being equal to or higher than the predetermined value.

3. The method for providing content as claimed in claim 1, wherein the providing comprises increasing a size of either one or both of the gaze content and content that is similar to the gaze content, and displaying either one or both of the gaze content and the content that is similar to the gaze content, in response to the preference for the gaze content being equal to or higher than the predetermined value.

4. The method for providing content as claimed in claim 1, further comprising:

determining a preference for a plurality of areas in the content UI; and displaying either one or both of the gaze content and content that is similar to the gaze content in an area having a high preference in the content UI in response to the preference for the gaze content being equal to or higher than the predetermined value.

5. The method for providing content as claimed in claim 4, further comprising displaying either one or both of the gaze content and the content that is similar to the gaze content in an area having a low preference in the content UI in response to the preference for the gaze content being lower than the predetermined value.

6. The method for providing content as claimed in claim 1, further comprising deleting or decreasing a size of either one or both of the gaze content and content that is similar to the gaze content, and displaying either one or both of the gaze content and the content that is similar to the gaze content, in response to the preference for the gaze content being lower than the predetermined value.

7. The method for providing content as claimed in claim 1, wherein the detecting comprises detecting the area at which the user gazes by tracking either one or both of a face direction and a movement of a pupil of the user.

8. The method for providing content as claimed in claim 1, wherein in response to the display apparatus being a 3D display apparatus, the measuring comprises measuring the brainwaves of the user using a brainwave measurer that is attached to 3D glasses that interlock with the 3D display apparatus.

9. The method for providing content as claimed in claim 1, wherein the determining further comprises determining the preference to be equal to or higher than a predetermined value in response to the measured brainwaves being a predetermined frequency while the user gazes at the gaze content for a predetermined period of time.

10. The method for providing content as claimed in claim 1, wherein the determining further comprises:

determining whether there are pre-stored brainwaves within a predetermined range of the measured brainwaves; and in response to the determining that there are pre-stored brainwaves within the predetermined range of the measured brainwaves, determining, as the preference for the gaze content, a user preference matching the pre-stored brainwaves within the predetermined range of the measured brainwaves.

11. The method for providing content as claimed in claim 1, wherein the determining further comprises:

in response to the measured brainwaves being a frequency while the user gazes at the gaze content for a predetermined period of time, storing the measured brainwaves of the frequency with a high user preference; and in response to the measured brainwaves being the frequency while the user gazes at the gaze content for the predetermined period of time, determining, as the preference for the gaze content, the high user preference stored with the stored brainwaves.

12. A display apparatus comprising:

a displayer configured to display a content user interface (UI) comprising a plurality of content;

a gaze area detector configured to detect an area at which a user gazes in the content UI;

a brainwave measurer configured to measure brainwaves of the user with respect to the detected area at which the user gazes; and a controller configured to:

determine a preference for gaze content that is present in the detected area at which the user gazes based on the measured brainwaves of the user; and control the displayer to provide the gaze content with a changed size or position based on the determined preference, wherein the controller is further configured to:

determine whether there are pre-stored brainwaves coinciding with the measured brainwaves;

in response to the controller determining that there are pre-stored brainwaves coinciding with the measured brainwaves, determine, as the preference for the gaze content, a user preference matching the pre-stored brainwaves; and in response to the user viewing specified content for a long period of time after brainwaves of a specified frequency are detected, except for a pre-stored frequency, store the detected brainwaves of the specified frequency that match a high preference.

13. The display apparatus as claimed in claim 12, wherein the controller is further configured to recommend content that is similar to the gaze content in response to the preference for the gaze content being equal to or higher than the predetermined value.

14. The display apparatus as claimed in claim 12, wherein the controller is further configured to increase a size of either one or both of the gaze content and content that is similar to the gaze content, and display either one or both of the gaze content and the content that is similar to the gaze content, in response to the preference for the gaze content being equal to or higher than the predetermined value.

15. The display apparatus as claimed in claim 12, wherein the controller is further configured to:

determine a preference for a plurality of areas in the content UI; and control the displayer to display either one or both of the gaze content and content that is similar to the gaze content in an area having a high preference in the content UI in response to the preference for the gaze content being equal to or higher than the predetermined value.

16. The display apparatus as claimed in claim 15, wherein the controller is further configured to control the displayer to display either one or both of the gaze content and the content that is similar to the gaze content in an area having a low preference in the content UI in response to the preference for the gaze content being lower than the predetermined value.

17. The display apparatus as claimed in claim 12, wherein the controller is further configured to delete or decrease a size of either one or both of the gaze content and content that is similar to the gaze content, and control the displayer to display either one or both of the gaze content and the content that is similar to the gaze content, in response to the preference for the gaze content being lower than the predetermined value.

18. The display apparatus as claimed in claim 12, wherein the gaze area detector is further configured to detect the area at which the user gazes by tracking either one or both of a face direction and a movement of a pupil of the user.

19. The display apparatus as claimed in claim 12, wherein in response to the display apparatus being a 3D display apparatus, the brainwave measurer is attached to 3D glasses that interlock with the 3D display apparatus.

\* \* \* \* \*